(12) United States Patent
Dinkler

(10) Patent No.: US 6,584,630 B1
(45) Date of Patent: Jul. 1, 2003

(54) RADIOLUCENT SURGICAL TABLE EXTENSION ASSEMBLY AND METHOD

(75) Inventor: Charles E. Dinkler, Cincinnati, OH (US)

(73) Assignee: Ohio Medical Instrument Company, Inc., Cincinnati, OH (US)

( * ) Notice: Subject to any disclaimer, the term of this patent is extended or adjusted under 35 U.S.C. 154(b) by 0 days.

(21) Appl. No.: 09/543,878

(22) Filed: Apr. 6, 2000

(51) Int. Cl.$^7$ ................................................ A61G 13/00

(52) U.S. Cl. .................................. 5/622; 5/640; 5/643

(58) Field of Search ........................... 5/601, 622, 632, 5/638, 621, 640, 643; 248/220.21, 220.22, 224.51

(56) References Cited

U.S. PATENT DOCUMENTS

| | | | |
|---|---|---|---|
| 1,171,713 A | 2/1916 | Gilkerson | |
| 2,707,662 A | 5/1955 | Goldfield et al. | |
| 2,753,233 A | 7/1956 | Rock | |
| 2,840,429 A | 6/1958 | McDonald | |
| 2,872,259 A | 2/1959 | Thorpe | |
| 3,428,307 A | 2/1969 | Hunter et al. | |
| 3,766,384 A | 10/1973 | Anderson | |
| 4,076,230 A | 2/1978 | Pike | |
| 4,333,638 A | 6/1982 | Gillotti | |
| 4,484,571 A | 11/1984 | Velazquez | |
| 4,506,872 A | 3/1985 | Westerberg et al. | |
| 4,584,731 A | 4/1986 | Carter | |
| 4,616,814 A | 10/1986 | Harwood-Nash et al. | |
| 4,669,106 A | 5/1987 | Ammerman | |
| 4,688,780 A | 8/1987 | Hanz | |
| 4,727,328 A | 2/1988 | Carper et al. | |
| 4,881,728 A | 11/1989 | Hunter | |

(List continued on next page.)

FOREIGN PATENT DOCUMENTS

| | | |
|---|---|---|
| EP | 0104591 A2 | 4/1984 |
| WO | WO9408704 | 4/1994 |
| WO | WO9911176 | 3/1999 |

OTHER PUBLICATIONS

F.W. Zonneveld, Ph.D., *Intraoperative CT Scanning in Brain Surgery: Implementation of the Tomoscan M Mobile CT Scanner*, Computed Tomography, Philips Medical Systems International B.V., pp. 1–7.

Philips, *Medicamundi*, vol. 42, Issue 1, Mar., 1998; pp. 1–32.

Primary Examiner—Teri Pham Luu
Assistant Examiner—Frederick Conley (57) ABSTRACT

A radiolucent surgical table extension assembly for use in combination with a scanning machine having an enclosed scanning zone. A radiolucent support member has a proximal end adapted to be removably attached to one end of a table in a cantilever fashion. The radiolucent support member has a rigidity sufficient to support an upper torso and head of a patient. The table and the radiolucent support member are movable relative to the scanning machine to locate the radiolucent support member and the head of the patient within the scanning zone. A radiolucent mounting structure is connected to the radiolucent support member, and a radiolucent head support is attached to the radiolucent mounting structure for supporting the head of the patient. The radiolucent head support has an opening extending therethrough. The opening receives a locking clamp for attaching the radiolucent head support to the radiolucent mounting structure. In one embodiment, the head support is a radiolucent skull clamp having two frame members wherein each of the members has first legs extending adjacent each other. The first legs have openings extending therethrough, and the openings receive a locking clamp for attaching the radiolucent skull clamp to the radiolucent mounting structure.

24 Claims, 5 Drawing Sheets

U.S. PATENT DOCUMENTS

| | | |
|---|---|---|
| 4,910,819 A | 3/1990 | Brown |
| 4,914,682 A | 4/1990 | Blumenthal |
| 4,944,501 A | 7/1990 | Sireul et al. |
| 4,989,849 A | 2/1991 | Zupancic et al. |
| 5,088,706 A | 2/1992 | Jackson |
| 5,090,044 A | 2/1992 | Kobayashi |
| 5,155,758 A | 10/1992 | Vogl |
| 5,177,823 A | 1/1993 | Riach |
| 5,233,713 A | 8/1993 | Murphy et al. |
| 5,276,927 A * | 1/1994 | Day .............................. 5/622 |
| 5,335,384 A | 8/1994 | Foster et al. |
| 5,347,668 A | 9/1994 | Manning |
| 5,427,436 A | 6/1995 | Lloyd |
| 5,475,884 A | 12/1995 | Kirmse et al. |
| 5,499,415 A | 3/1996 | McKenna |
| 5,537,704 A * | 7/1996 | Dinkler ........................ 5/622 |
| 5,560,728 A | 10/1996 | McFadden |
| 5,655,238 A | 8/1997 | Stickley et al. |
| 5,661,859 A | 9/1997 | Schaefer |
| 5,675,851 A | 10/1997 | Feathers |
| 5,758,374 A | 6/1998 | Ronci |
| 5,774,916 A | 7/1998 | Kurhi |
| 6,003,174 A * | 12/1999 | Kantrowitz et al. ........... 5/601 |

* cited by examiner

RADIOLUCENT SURGICAL TABLE EXTENSION ASSEMBLY AND METHOD

FIELD OF THE INVENTION

This invention relates to neurosurgical apparatus generally, and more particularly, to an improved apparatus for supporting an upper torso and head of a patient.

BACKGROUND OF THE INVENTION

With current medical practices, it is common for a patient to undergo a diagnostic scanning procedure, which is normally performed in a separate suite containing the scanning machine and dedicated to scanning procedures. The scanning machine may be a CT, MRI, or other scanning device. Thereafter, the scan data is utilized in a surgical planning process, which conventionally takes place at a location, for example, an office or an operating room. In some surgical procedures, the scanning data is utilized with a system for post processing the scan data acquired during imaging. Further, the imaging system may be located in a surgical suite, and the surgical planning performed before and during a surgical procedure utilizing the imaging system and scan data.

During the scanning procedure, the patient must maintain a perfectly still and motionless posture, and while most often, the patient simply lies on a scanning support table, in some situations, the patient may be supported in the desired scanning position with pads, straps or other supports. Further, the support on which the patient rests is normally radiolucent, that is, transparent to the scanning device, so that the support does not compromise the utility of the scanned image. Further, the patient support used for scanning normally translates with respect to the imaging device. Translation of the patient support permits the patient to be moved into the scanning field or zone of the scanning machine.

After the scanning process is completed, often the patient is then moved to an operating room which requires either that the patient walk, or be carried, for example, by transferring the patient from the scanning table to an operating table. Alternatively, as illustrated in U.S. Pat. No. 5,475,884, the patient may be supported on a portable support plate, which is easily moved between the scanning table and the operating table. The scan data is often used in a post processing imaging system for surgical planning purposes both prior to and during surgery. If during or after a surgical process, it is desired to scan a patient again, the patient must be moved from the operating room to the scanning suite, transferred to and from the operating table to the scanning table, and after scanning, transferred back to the operating table and returned to the operating room. The above process is cumbersome, time consuming and potentially risky for the patient.

Some newer scanning machines are substantially reduced in size. One such machine is shown in FIGS. 2 and 3 of U.S. Pat. No. 5,499,415, which show an annular-shaped scanner mounted on a wheel-supported frame, to enable the scanner to be used at multiple sites. Consequently, such scanning machines do not require their own suite or room, but instead, they may be used within the operating suite itself. Thus, in an operating room, the patient may be scanned; the surgical planning performed; an operative procedure executed; and the patient scanned again to determine the current status of the operative procedure. Based on the new scanned images obtained from the one or more "interoperative" scans, the operative procedure can be continued and the above process repeated as necessary.

A limitation of the current state-of-the-art is that the posture of the patient during the scanning process is often different from the patient's posture during surgery. If a patient is positioned in one posture on a scanning table during the scanning process, and then is moved to an operating table, that motion of the patient may cause the position of the target to change with respect to the body surface. During surgery, this problem is compounded by tissue shifts attendant to the opening of body cavities, removal of body fluid or tissues and tissue retractions. Thus, while such motion may be small, any motion of the target will reduce or compromise the utility of the preoperative scan data.

The solution to these problems is to scan the patient in the operating room during surgery while the patient is maintained in the surgical posture, and further, to make successive interoperative scans, as necessary, while still holding the patient in the same surgical posture.

While current scanning tables are radiolucent and provide a translation to move the patient into the scanning machine, such scanning tables do not have the accessories required to attach, support and stabilize surgical instrumentation and to properly support the patient's body in the desired surgical posture. Further, while surgical, or operating, tables contain numerous accessories and couplings to which surgical instrumentation may be attached and supported, most operating tables are not compatible with scanning instrumentation. Thus, as presently known, scanning tables cannot be used as operating tables, and generally, operating tables are inappropriate for use as scanning tables.

It is an object of this invention to overcome the above-described limitations in the prior art, by facilitating the function of supporting a patient in a desired position in a manner which readily accommodates successive surgical and scanning procedures as well as interoperative scans. Further the invention fulfills a need to improve and simplify surgical tooling used to support a patient during such procedures.

SUMMARY OF THE INVENTION

The present invention provides an improved radiolucent surgical table extension assembly for mounting a skull clamp to the table extension. The improved radiolucent surgical table extension assembly of the present invention has fewer parts, is simpler to use, is more flexible and is generally less expensive and more reliable than known devices. The improved radiolucent surgical table extension assembly of the present invention is especially useful for mounting a head support, for example, a radiolucent skull clamp, to the surgical table extension and permits neurological surgical procedures to be performed more efficiently and with less stress.

In accordance with the principles of the present invention and the described embodiments, the invention is a radiolucent surgical table extension assembly for use in combination with a scanning machine having an enclosed scanning zone. The invention includes a radiolucent support member having a proximal end adapted to be removably attached to one end of a table in cantilever fashion. The radiolucent support member has a rigidity sufficient to support an upper torso and head of a patient. The table and the radiolucent support member are movable relative to the scanning machine to locate the radiolucent support member and the head of the patient within the scanning zone. A radiolucent mounting structure is connected to the radiolucent support member, and a radiolucent head support is attached to the radiolucent mounting structure for supporting the head of the patient. The radiolucent head support has an opening extending therethrough. The opening receives a locking clamp for attaching the radiolucent head support to the radiolucent mounting structure.

In one aspect of this embodiment, the mounting structure permits the head support to be moved through linear and rotary motions with respect to the support member. In another aspect of this embodiment, the head support is a radiolucent skull clamp having two frame members, wherein each of the members has first legs extending adjacent each other. The first legs have openings extending therethrough for receiving the locking clamp to attach the radiolucent skull clamp to the radiolucent mounting structure.

In another embodiment of the invention, the skull clamp includes a first frame member having an angular positioning mechanism mounted at one end of the first frame member with a pin holding member rotatably mounted to the angular positioning mechanism. A first arm forming an opposite end of the first frame member, the first arm has an opening extending therethrough. A second frame member has a pin holder on one end thereof and a first arm forming an opposite end of the second frame member. The first arm has an opening extending therethrough, and the first arms of the first and second frame members are positioned with respect to each other so that the first and second frame members form a generally C-shaped skull clamp. A clamp extends through the openings in the first arms of the first and second frame members and is adapted to removably connect the skull clamp to a supporting structure.

In one aspect of this second embodiment, the clamp is a knob attached to a threaded shaft; the opening in the first arm of the first frame member is a clearance hole for receiving the shaft; and the opening in the first arm of the second frame member is a clearance slot for receiving the shaft.

In a further embodiment, the present invention includes a method of mounting a radiolucent skull clamp having a connector to a support having a mating connector. The method first holds the connector of the radiolucent skull clamp against the connector of the support in a desired orientation. A clamp shaft is then inserted through clearance holes in both the first and second frame members of the skull clamp, and the clamp shaft is then secured to the support, thereby mounting the skull clamp to the support.

The improved radiolucent surgical table extension assembly of the present invention utilizes a radiolucent skull clamp with clearance openings extending through the base of the adjacent lower arms of the clamp with the movable lower arm having a clearance slot, thereby permitting the movable lower arm to move through its full range of motion without interfering with a clamp shaft extending through the clearance openings and mounting the skull clamp to the table extension.

Various additional advantages, objects and features of the invention will become more readily apparent to those of ordinary skill in the art upon consideration of the following detailed description of the presently described embodiments taken in conjunction with the accompanying drawings.

DETAILED DESCRIPTION OF THE INVENTION

Figure 1:
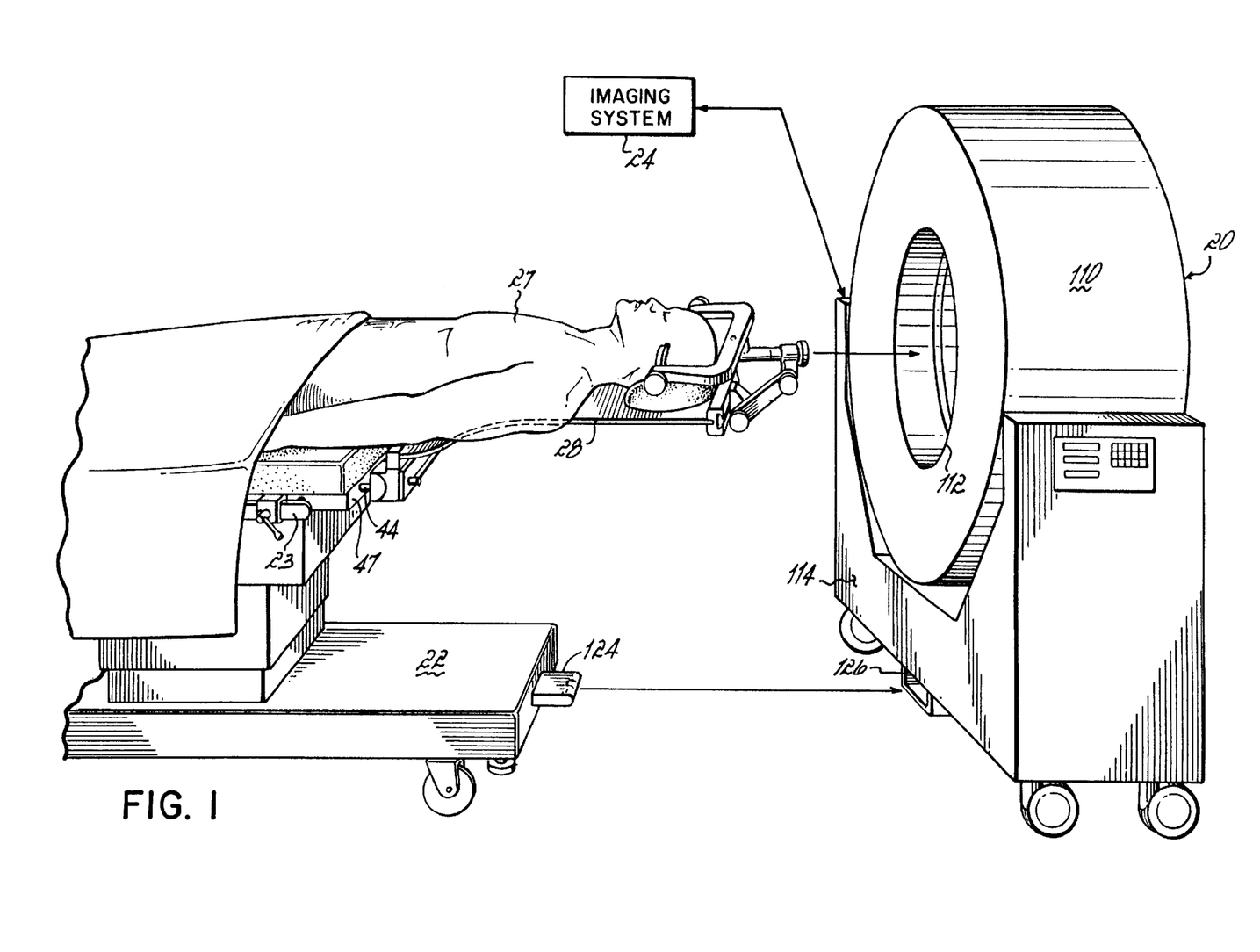
FIG. 1 is a perspective view of a portion of a known surgical table including a radiolucent table extension assembly.

Referring to FIG. 1, a portable CT scanning system 20 is located in an operating suite with an operating table 22. The CT scanning system may be either a mobile system such as that commercially available from Analogic of Peabody, Massachusetts or a stationary scanning system such as that commercially available from General Electric Medical Systems of Milwaukee, Wis. The operating table 22 may be one of many commercially available tables, for example, an operating table commercially available from Amsco of Erie, Pa., MDT Diagnostic Co. of N. Charleston, N.C., or other suppliers. The operating table has a lateral rail 23 extending along each side of the table to which retractors, clamps and other devices may be attached in a stable manner. A stereotactic image processing system 24, for example, the MAYFIELD-ACCISS image processing system, commercially available from Ohio Medical Instrument Company, Inc. of Cincinnati, Ohio is operatively connected to the scanner 20 and responsive to scan data provided by the CT system 20 to provide selected images on a display screen of the scan data along selected planes. Use of an imaging system 24 of this type is described in U.S. Pat. No. 5,695, 501, which is expressly incorporated by reference herein, in its entirety. To facilitate the use of the operating table 22 with the CT system 20, one end of the operating table is used to support a radiolucent support member or table extension 28.

In use, referring to FIG. 1, the scanning system 20 and operating table 22 are brought into a surgical suite. The scanning system 20 has a toroid shape scanning element 110 with a central opening 112 defining an enclosed or encircled scanning zone with which the portion of the patient to be scanned is axially aligned. The scanning element 110 further has the capability of rotating or tilting within its base 114 with respect to a diametric horizontal axis. The distal end of the support plate 28 is narrowed so that it can extend into the opening 112 without interference. If necessary, the head section (not shown) of the table 22 is removed therefrom, and the radiolucent table extension 28 is mounted to the table by inserting the support bars 44 into mating bores on the end surface 47 of the table 22. The patient 27 is then positioned on the table in a posture suitable for a surgical procedure. The length of the support plate 28 is sized such that the patient's upper torso and head are accessible for scanning and surgical procedures. The portion of the patient's anatomy on which the surgical procedure is to be performed may be stabilized by various clamps and restraining devices. Further, the support plate 28 or the scanning element 110 may be tilted so that the desired posture and/or scanning plane is achieved.

When the desired surgical posture is achieved, normally the patient will have already been scanned; and the surgical planning and procedure can be performed. Thereafter, a portion of the radiolucent table extension 28 is then moved into the opening 112, for a follow-up scan. The extent to which the extension 28 is moved into the opening 112 depends on what portion of the head or upper torso is to be scanned. The initial alignment of the table extension may be determined by visual inspection; and thereafter, a scan made to determine exactly whether, and to what extent, the table extension may be out of alignment. Alternatively, the scanner may be equipped with LED's, or other sources of light, providing beams of light with which the table extension can be aligned. In another embodiment, the table 22 may have an alignment tab 124 which is moved into an alignment slot 124 on the scanner 110. When the tab 124 is properly seated in the slot 126, the table is properly aligned with the scanner 110. The scanning process is executed by the scanning machine moving the scanning element 110 incrementally in an axial direction and with each increment, a scan is taken. Thereafter, the extension 28 and the patient are removed from within the scanning element 110, either by moving the scanning machine 20 or the operating table 22. The scan data is then used in association with the imaging system 24 to plan the surgical procedure. The surgical procedure is then performed, and thereafter, the patient may be moved back into the scanning machine 20, and the scanning process repeated. The scanning and imaging system may be used to gauge the effectiveness of the surgical procedure; and if necessary, further procedures performed. The above process may be executed any number of times with the patient remaining in the desired position on the same patient support.

Thus, the above-described operating table and radiolucent table extension has a significant advantage of not only being able to support a patient during a scanning process, but also support the patient in the identical posture during a surgical procedure. The radiolucent table extension permits an operating table that is normally nonradiolucent and inappropriate for scanning purposes to be used with a scanning machine. Further, the table extension may be tilted to accommodate different desired surgical postures and is sized and shaped to readily fit within the opening of a scanning element, whether in a horizontal or tilted position. Further, not only does the table position permit successive scanning and operative procedures on the upper torso and head of a patient, but the radiolucent table extension 28 readily supports the patient in a prone, or supine position. The above described system is illustrated in more detail in U.S. Pat. No. 6,003,174, is assigned to the assignee of the present invention and is hereby incorporated in its entirety by reference herein.

Figure 2:
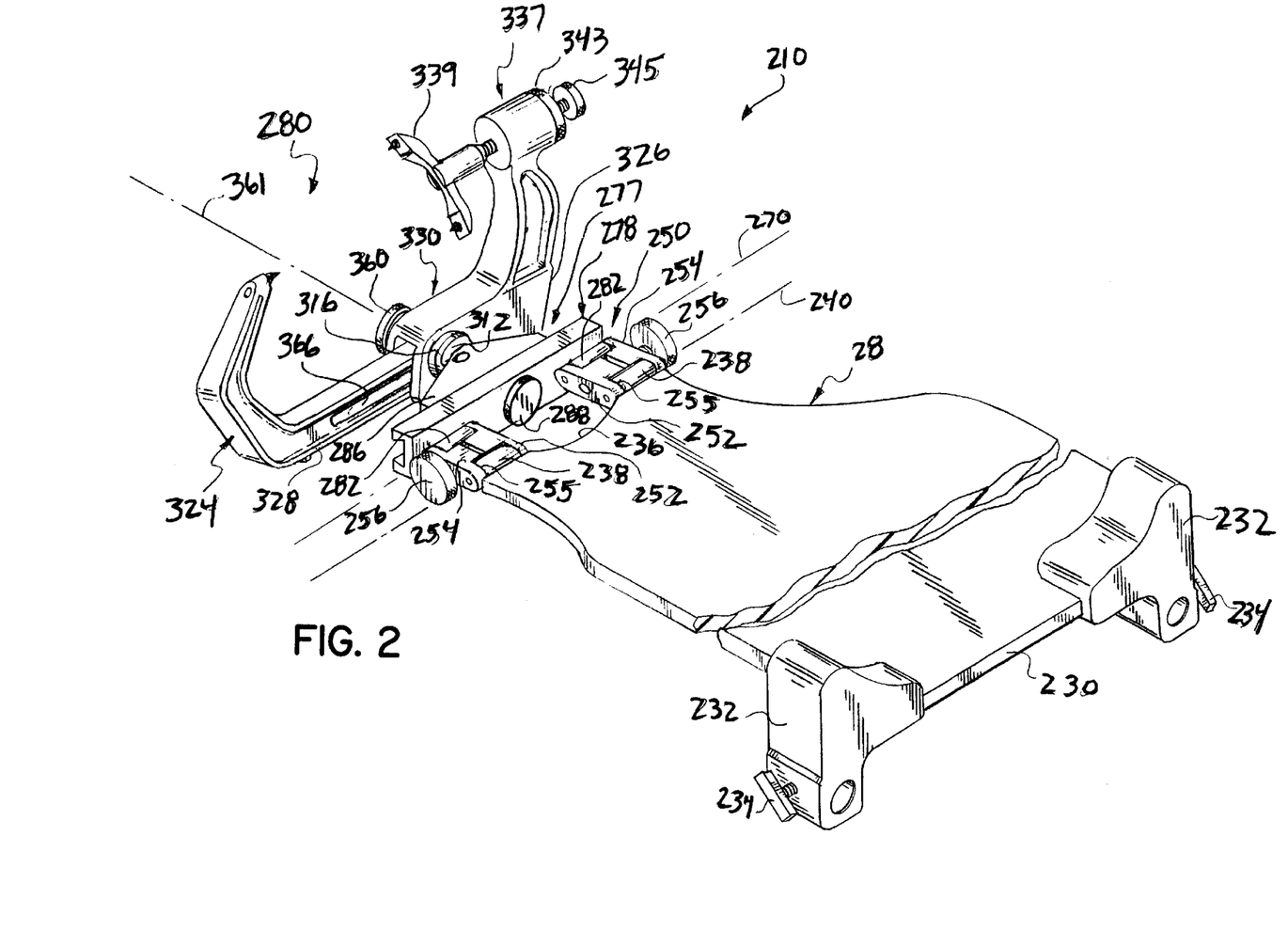
FIG. 2 is a first perspective view of a radiolucent skull clamp in accordance with the principles of the present invention.

While the above described system has significant utility, there is a continuing effort to improve and simplify the mounting of tooling, clamps and other devices to the radiolucent table extension. An improved system for mounting a radiolucent head clamp to the radiolucent table extension 28 is illustrated in FIG. 2. A first, or inboard, end 230 of the table extension 28 connects to the surgical table 22 (FIG. 1). Normally, this connection at the first end 230 occurs via a pair of spaced base mounts 232. Each of the base mounts 232 engages an inboard corner of the radiolucent table extension 28 and is shaped to receive an outwardly extending post or bar 43 (FIG. 1) extending from the surgical table 22. A threaded knob 234 tightens upon the inserted post on both sides of the surgical table 22 to securely mount the extension 28. The extension 28 comes in two different lengths. Depending on the length of the extension 28 and the type of table 22, the manner of mounting the extension 28 may vary.

A second, or outboard, end 236 of the radiolucent table extension 28 includes a pair of spaced radiolucent collars 238 aligned along a first connection axis 240. The first axis 240 is oriented horizontally and perpendicular to the longitudinal direction of the radiolucent table extension 28. The first connection axis 240 provides for hinged, or pivotal, movement of the radiolucent adaptor assembly 210, and everything else connected thereto, relative to the radiolucent table extension 28.

To provide this hinged movement about the first connection axis 240, the radiolucent adaptor assembly 210 comprises a pair of spaced radiolucent adaptor subassemblies 250, each of the adaptor subassemblies 250 is associated with one of the spaced collars 238 of the table extension 28. Each subassembly 250 includes identically shaped, radiolucent interior and exterior pieces 252, 254, respectively, which are tightenable in a horizontal direction via a threaded knob 256. The knob 256 includes a threaded shaft (not shown) which extends through a central clearance bore (not shown) in the exterior piece 254 and engages a central threaded bore (not shown) in the interior piece 252. If desired, the arrangement of the respective interior and exterior pieces 252, 254 can be reversed, so long as the pieces 252, 254 are tightenable together upon the respective collars 238.

Along first axis 240, each of the interior and exterior pieces 252, 254, respectively, has a pair of parallel locator pins (not shown). The locator pins are sized to extend through clearance bores in the collars 238 along the connection axis 240, with a slip fit, so as to be rotatable relative to the collars 238. Together, the opposing locator pins of the respective interior and exterior pieces 252, 254 are held by the collars 238 along the first connection axis 240, so that upon tightening of each of the threaded knobs 256, the inwardly directed surfaces of the interior and exterior pieces 252, 254 engage the outwardly directed surfaces of the respective collars 238. Normally, the annular end surfaces 255 of the collars 238 are toothed or have a known starburst connector, and the inwardly directed opposed surfaces of respective interior and exterior pieces 252, 254 likewise have correspondingly shaped serrations. A starburst connector as referred to herein is normally a circular structure in which the connector portion is an annular ring of adjacent, radially extending serrations or teeth.

Thus, upon sufficient tightening of threaded knobs 256, the respective interior and exterior pieces 252, 254 will move together horizontally until their respective engagement surfaces contact and engage opposing surfaces of the respective collars 238. This engagement force holds the radiolucent adaptor subassemblies 250 in a fixed position relative to the radiolucent table extension 28. Upon loosening the threaded knobs 256, the subassemblies 250 may be hingedly moved relative to first connection axis 240 to a different position, whereupon the threaded knobs 256 can again be tightened to form a rigid connection.

Figure 4:
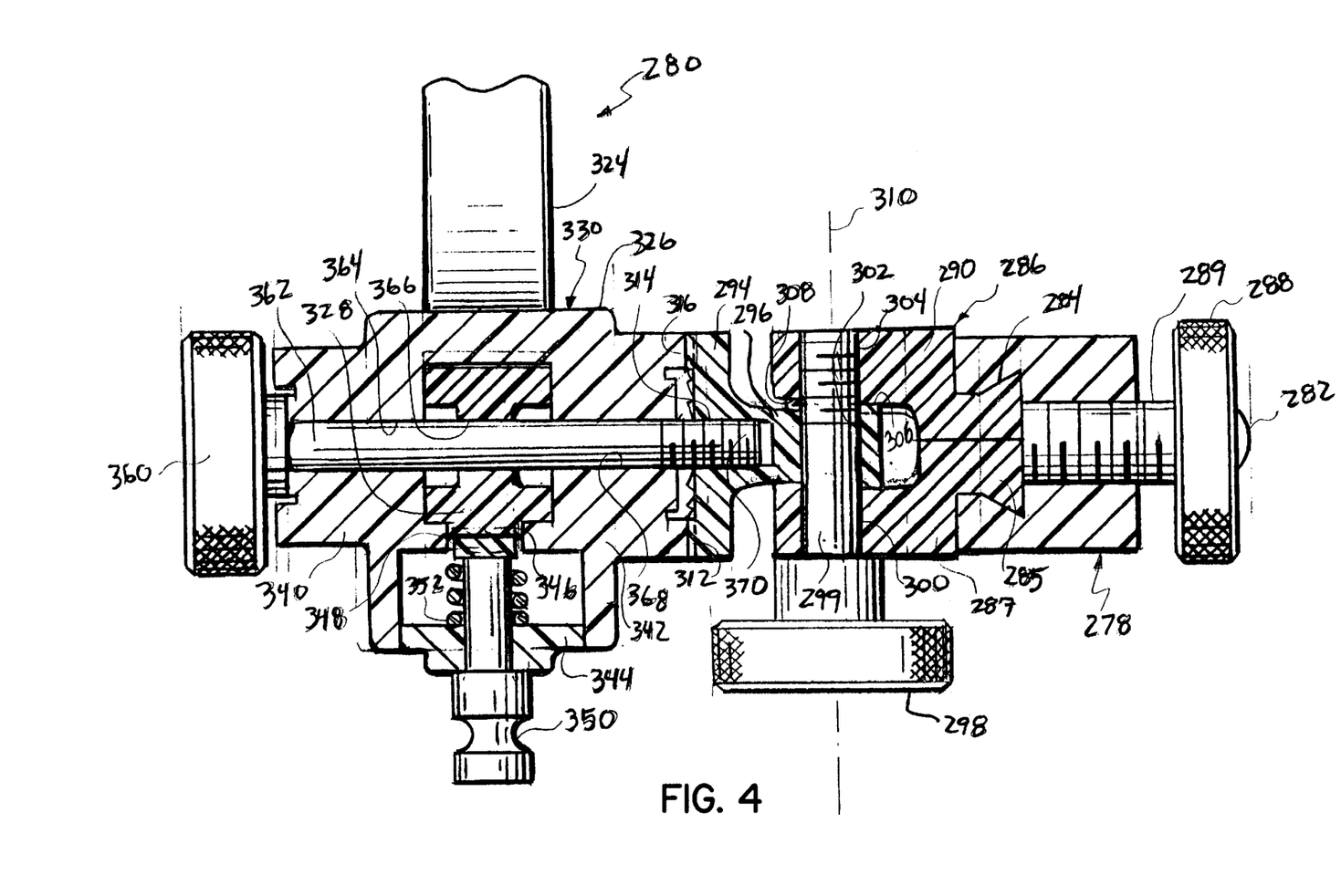
FIG. 4 is a cross-section view taken along the line 4—4 of FIG. 3.
Figure 5:
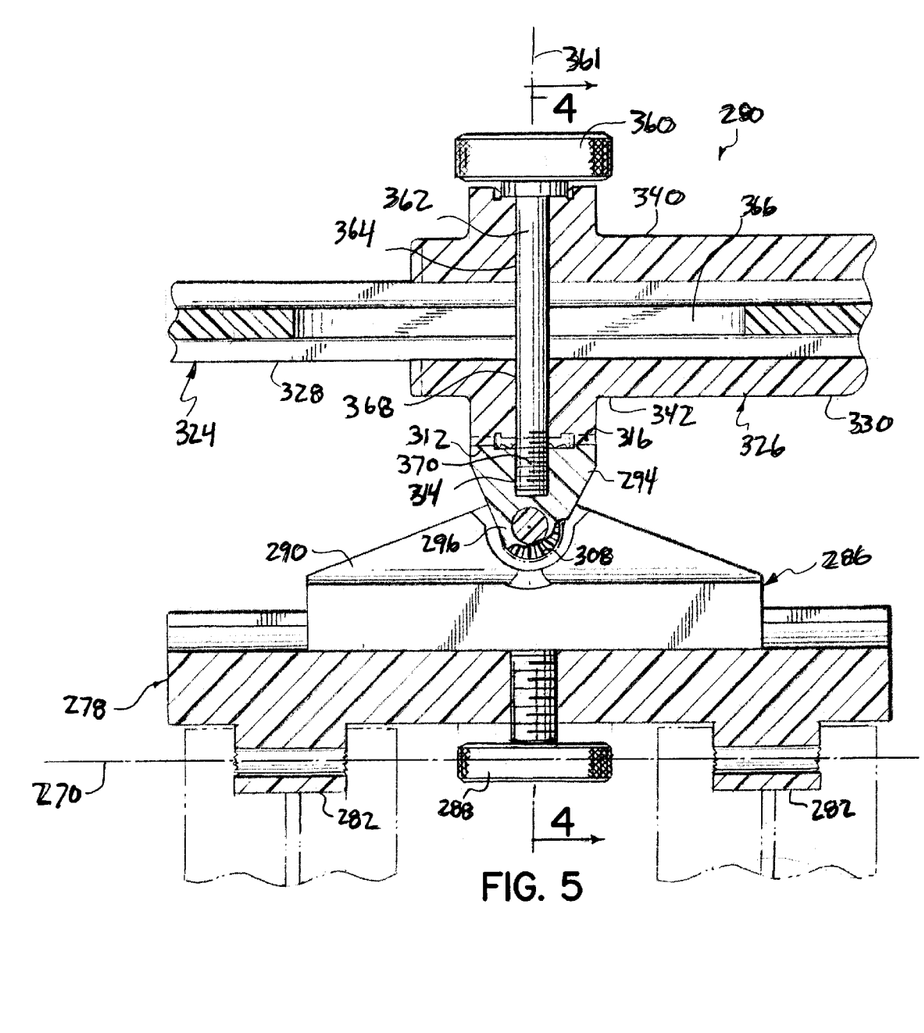
FIG. 5 is a cross-section view taken along the line 5—5 of FIG. 4.

The radiolucent adaptor assembly 210 of the present invention includes a radiolucent mounting structure 277 which releasably holds and supports a head support 280, for example, a radiolucent skull clamp. The radiolucent mounting structure 277 includes a radiolucent bracket 278, a radiolucent sliding member 286 and a radiolucent pivoting member 294. The mounting structure 277 permits the skull clamp 280 to be moved through linear and rotary motions with respect to support member 28. The radiolucent bracket 278 includes a pair of spaced collars 282 which are adapted to be connected to the spaced adaptor subassemblies 250 along the second connection axis 270. This likewise enables the skull clamp 280 to be oriented in a desired position relative to the table extension 28, via hinged movement about first connection axis 240, hinged movement about second connection axis 270, or both. Referring to FIG. 4, the radiolucent bracket 278 includes an internal dovetail 284 sized to receive a complementary shaped dovetail member 285 from a radiolucent sliding member 286. The radiolucent sliding member 286 is lockable to the radiolucent bracket 278 via a clamp comprised of an adjustment knob 288 and threaded shaft 289. The end of the shaft 289 pushes and clamps the dovetail member 285 against the dovetail member 284.

The sliding member 286 is comprised of first and second radiolucent connector members 287, 290 that together form a generally U-shaped bracket or clevis. The sliding member 286 further includes a radiolucent pivoting member 294 having a tongue 296 extending within the clevis between the connecting members 287, 290. A clamp having a radiolucent locking knob 298 also includes a shaft 299 that extends through a clearance hole 300 within the connecting member 287, through a clearance hole 302 of the tongue 296 and into a threaded hole 304 of the connecting member 290. An annular surface 306 on the upper side of the tongue 296 and an opposing lower surface 308 (FIG. 4) of the connector 290 are serrated or toothed to prevent relative angular motion between the pivoting member 294 and the sliding member 286 when the knob 298 is tightened. The pivoting member 294 has a known annular toothed or starburst connector 312 with a centrally located threaded hole 314. A mating starburst connector 314 extends from a frame member 326 of the skull clamp 280.

Referring to FIG. 2, the radiolucent surgical skull clamp 280 includes a C-shaped frame comprised of frame members 324, 326 which are movable to "telescope" toward and away from one another. The frame members 324, 326 of the clamp 322 are normally made of a radiolucent polyethersulfone (PES) and carbon composite material with the carbon component being about 30 percent of the composite by weight. Such a composite material is available from ICI Advanced Materials of Exton, Pa. under the commercial name "THERMOCOMP" JC-1006, and is also available from LNP Engineering Plastics of Thorndale, Penn. under the commercial name "STAT-KON" JC-1006. Alternatively, other radiolucent materials may be used.

Frame members 324, 326 have parallel first arms 328, 330, respectively, which are juxtaposed to each other in a sliding relationship with the first arm 330 of the frame member 326 cradling or surrounding the first arm 328 of the frame member 324. Extending from one end of the arm 328, the frame member 324 has an intermediate arm 332 extending diagonally away from the frame member 326 and an upper arm 334 extending angularly back toward the frame member 326. The upper arm 334 has, at its outer or distal end, a pin holder, for example, a threaded bore that receives a skull pin 335. Similarly, extending from the first arm 330, the frame member 326 has an intermediate arm 336 extending away from the frame member 324 and an upper arm 338 extending back toward the frame member 324. The upper arm 338 has an angular positioning mechanism 337 mounted at its outer or distal end. The angular positioning mechanism releasably locks a pin holding clevis 339 that supports skull pins 341. The clevis 339 and skull pins 341 are positioned by operating knobs 343, 345 in a known manner.

Figure 3:
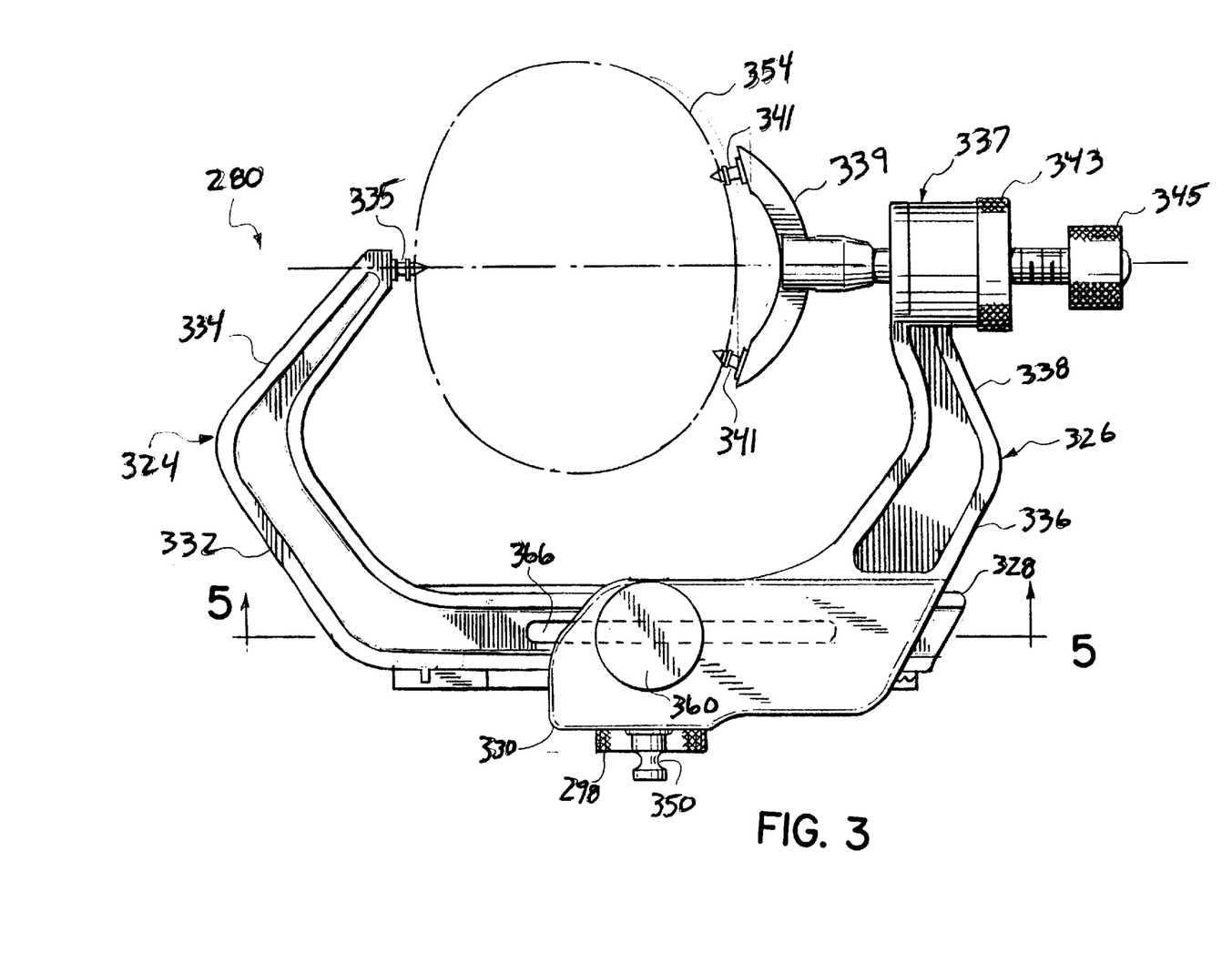
FIG. 3 is a front elevation view of the radiolucent skull clamp of FIG. 2.

Referring to FIG. 3, the first arm 330 of the frame member 326 is generally U-shaped to receive the first arm 328 of the frame member 324. The first arm 330 has two sides 340, 342, which extend past the first arm 328. A bottom plate 344 normally made from the PES and composite material is mounted between the sides 340, 342 of the first arm 330 such that there is clearance between the bottom plate 344 and a rack 346 on the bottom of the first arm 328. The bottom plate 344 is held in place between the sides 340, 342 of the first arm 330 by fasteners (not shown) which are normally made of nylon. The bottom plate 32 slidably receives a retractable rack member 348 which is connected to a release pin 350. The retractable rack member 348 and release pin 350 are normally made from the "DELRIN" acetal polymer material. The retractable rack member 348 has teeth that are sized to engage teeth of the rack 346 on the first arm 328 of frame member 324. A compression spring 352 is mounted over the release pin 350 and extends between the releasable rack member 348 and the bottom plate 344. The compression spring 352 applies a force against the retractable rack 348 which holds its teeth in engagement with the teeth of the rack 346 on the first arm 328, thereby preventing the frame members 324, 326 from moving in a direction away from each other. However, the configuration of the racks 346, 348 permits frame members 324, 326 to be slid toward each other to size or position the clamp 322 generally with respect to a patient's head 354, shown in phantom in FIG. 1. To release the clamp, the release pin 350 is pulled downward, thereby compressing the spring 352 and moving the rack 348 out of engagement with the rack 346 of the first arm 328. With the racks 346, 348 disengaged, the frame members 324, 326 may be separated, thereby releasing the clamp from the patient's head 354. Other details of the construction of the radiolucent skull clamp 280 are found in U.S. Pat. No. 5,537,704 assigned to the assignee of the present invention and hereby incorporated herein in its entirety.

Referring to FIG. 4, the radiolucent skull clamp 280 is attached to the pivoting member 294 of the sliding member 286 by means of a clamp comprised of a knob 360 and threaded shaft 362. The knob 360 has a threaded shaft 362 that extends through a clearance hole 364 in the side wall 340 at the first arm 330. The shaft 362 then extends through a slot 366 extending through the first arm 328 of the first frame member 324. The slot 366 is of a length that the shaft 362 does not interfere with the motion of the frame members 324, 326 over their full range of motion. The shaft 362 further extends through a clearance hole 368 of the second wall 342 of the first arm 330 of the frame member 326. The threaded distal end 370 of the shaft 362 threadedly engages the threaded hole 314 of the pivoting member 294, thereby locking the skull clamp to the sliding member 286, connecting element 287 and radiolucent table extension 28. While the holes 364, 368 are normally clearance holes, as will be appreciated, the shaft 362 may be threaded over its length; and one or both of the holes 364, 368 may be threaded holes.

In use, referring to FIGS. 2 and 4, the bracket 278 and sliding member 286 are first assembled onto the collars 238. Next, the skull clamp 280 is mounted onto the sliding member 286 using the knob 360 to tighten the skull clamp to a locked position determined by starburst connectors 312, 314. The precise location of the skull clamp 280 is adjusted in a plane generally perpendicular to the frame members 324, 326 using the adjustments associated with the knobs 288, 298, 360. Loosening the knob 288 permits the skull clamp 280 and sliding member 286 to be moved linearly in a direction that is substantially horizontal and parallel to a plane passing through the frame members 324, 326. When the skull clamp 280 is at the desired position, tightening the knob 288 locks the sliding member 286 to the bracket 278. Loosening the knob 298 permits the skull clamp 280 to be pivoted about an axis of rotation 310 that is normally vertical and substantially parallel to the plane passing through the frame members 324, 326. After the desired orientation about the axis 310 is found, the knob 298 is tightened to lock the skull clamp 280 at that orientation. Loosening the knob 360 permits the skull clamp 280 to be pivoted about an axis of rotation 361 that is normally horizontal and substantially perpendicular to the plane passing through the frame members 324, 326. After the desired orientation about the axis 361 is found, the knob 360 is tightened to lock the skull clamp 280 at that orientation. The height and angle of the skull clamp 280 is further precisely adjusted using the knobs 256. The knobs 256 on both sides of the table extension 28 are normally tightened or loosened in unison, to facilitate orienting the radiolucent support 264 relative to the table extension 28. As with the connections along the first connection axis 240, along the second connection axis 270, each adaptor subassembly 250 includes opposing locator pins 271 which extend along the second axis 270 and into the collars 282, to locate the interior and exterior pieces 252, 254 in a desired position relative to the second axis 270.

The radiolucent adaptor assembly 210 provides two parallel axes of connection 240, 270 residing between the radiolucent table extension 28 and the patient stabilization device used to hold the head of the patient in a desired position. Thus, the present invention increases the versatility of patient positioning relative to a radiolucent table extension assembly for advantageous use in interoperative scanning procedures. This versatility is available for patient stabilization with either a skull clamp or a horseshoe headrest. In fact, this invention makes it easy for attendants to interchange the surgical set up, by removing one of these two different holding devices and connecting the other. Moreover, the present invention achieves these advantages in a manner which is user-friendly for the surgeon and operating room attendants, because the maneuverability of the patient stabilization device is achieved about two spaced parallel axes 240, 270 via adjustment of a pair of spaced adjustment knobs 256.

The interior pieces 252, 254 and the locator collars 238, 282 along the first and second connector axes 240, 270 are made by Potts Composites of Floydada, Tex. out of carbon fiber composite and epoxy resin material. The knob 256 are made from aluminum or a radiolucent material.

Thus, the improved radiolucent surgical table extension assembly of the present invention simplifies the mounting of a radiolucent skull clamp to the table extension. The improved radiolucent surgical table extension assembly of the present invention has fewer parts, is simpler to use, is more flexible and is generally less expensive and more reliable than known devices. The improved radiolucent surgical table extension assembly of the present invention is especially useful for mounting a radiolucent skull clamp to the surgical table extension and permits neurological surgical procedures to be performed more efficiently and with less stress.

While the present invention has been illustrated by a description of various described embodiments and while these embodiments have been described in considerable detail in order to describe the best mode of practicing the invention, it is not the intention of Applicant to restrict or in any way limit the scope of the appended claims to such detail. Additional advantages and modifications within the spirit and scope of the invention will readily appear to those skilled in the art. For example, in the described embodiment, the head support 280 is shown as a skull clamp. As will be appreciated, a horseshoe headrest, other types of headrests, a single piece skull clamp or other types of head supports may be connected to the mounting structure 277.

Further, in the described embodiment, the various clamps are implemented with knobs and associated threaded shafts. As will be appreciated, other mechanical clamping devices or mechanisms may be used. Further, the described mounting structure 277 provides a serial linkage of a bracket 278, a sliding member 286 and a pivoting member 294. As will be appreciated, the arrangement of the sliding member 286 and pivoting member 294 may be reversed. Further, other relatively moving members may be used to obtain motion in other directions. While it is anticipated that the greatest utility of a skull clamp having openings 366, 364, 368 in the respective lower arms 328, 330 is one made from radiolucent materials. As will be appreciated, the structure described and claimed herein can also be applied to devices made of opaque materials.

Therefore, the invention in its broadest aspects is not limited to the specific detail shown and described. Consequently, departures may be made from the details described herein without departing from the spirit and scope of the claims which follow.

What is claimed is:

1. A radiolucent surgical table extension assembly for use in combination with a scanning machine having an enclosed scanning zone, comprising:

a radiolucent support member having a proximal end adapted to be removably attached to one end of a table in cantilever fashion, the radiolucent support member having a rigidity sufficient to support an upper torso and head of a patient, the table and the radiolucent support member adapted to be movable relative to the scanning machine to locate the radiolucent support member and the head of the patient within the scanning zone;

a radiolucent mounting structure connected to the radiolucent support member; and a radiolucent skull clamp attached to the radiolucent mounting structure and adapted to support the head of the patient, the radiolucent skull clamp having two frame members with respective first legs extending adjacent each other, the first legs having respective openings extending therethrough, and the openings receiving a mounting clamp for attaching the radiolucent skull clamp to the radiolucent mounting structure.

2. A radiolucent surgical table extension assembly for use in combination with a scanning machine having an enclosed scanning zone, comprising:

a radiolucent support member having a proximal end adapted to be removably attached to one end of a table in cantilever fashion, the radiolucent support member having a rigidity sufficient to support an upper torso and head of a patient, the table and the radiolucent support member adapted to be movable relative to the scanning machine to locate the radiolucent support member and the head of the patient within the scanning zone;

a radiolucent mounting structure connected to the radiolucent support member and comprising a radiolucent bracket pivotally mounted to a distal end of the radiolucent support member to provide pivoting motion with respect to a first substantially horizontal axis of motion; and a radiolucent skull clamp attached to the radiolucent mounting structure and adapted to support the head of the patient, the radiolucent skull clamp having two frame members wherein each of the members has first legs extending adjacent each other, the first legs having respective adjacent openings extending therethrough, and the openings receiving a locking clamp for attaching the radiolucent skull clamp to the radiolucent mounting structure.

3. The surgical table extension of claim 2 wherein the radiolucent mounting structure comprises relatively movable parts permitting the skull clamp to be moved through linear and rotary motions with respect to the radiolucent support member.

4. The surgical table extension of claim 2 wherein the radiolucent mounting structure comprises parts permitting the skull clamp to be moved with respect to the radiolucent support member.

5. The surgical table extension of claim 4 wherein the parts of the radiolucent mounting structure permit the skull clamp to be pivoted with respect to an axis of rotation substantially parallel to a plane defined by the frame members of the skull clamp.

6. The surgical table extension of claim 4 wherein the parts of the radiolucent mounting structure permit the skull clamp to be pivoted with respect to an axis of rotation substantially perpendicular to a plane defined by the frame members of the skull clamp.

7. The surgical table extension of claim 4 wherein the parts of the radiolucent mounting structure permit the skull clamp to be moved linearly along an axis of motion substantially parallel to a plane defined by the frame members of the skull clamp;

pivoted with respect to an axis of rotation substantially parallel to a plane defined by the frame members of the skull clamp; and pivoted with respect to an axis of rotation substantially perpendicular to a plane defined by the frame members of the skull clamp.

8. The surgical table extension of claim 2 wherein the radiolucent mounting structure comprises parts permitting the skull clamp to be moved through linear and rotary motions with respect to the radiolucent support member.

9. The surgical table extension of claim 8 wherein the parts of the radiolucent mounting structure permit the skull clamp to be moved linearly along an axis of motion substantially parallel to a plane defined by the frame members of the skull clamp.

10. The surgical table extension of claim 2 wherein the radiolucent bracket is pivotally mounted to the distal end of the radiolucent member to provide pivoting motion with respect to a second substantially horizontal axis of motion.

11. The surgical table extension of claim 2 wherein the radiolucent mounting structure further comprises a radiolucent sliding member slidingly mounted to the radiolucent bracket.

12. The surgical table extension of claim 11 wherein the radiolucent mounting structure further comprises a clamp for releasably locking the sliding member at a desired position with respect to the radiolucent bracket.

13. The surgical table extension of claim 12 wherein the radiolucent sliding member moves in a direction substantially parallel to a plane passing through the frame members of the radiolucent skull clamp.

14. The surgical table extension of claim 11 wherein the radiolucent mounting structure further comprises a radiolucent pivoting member rotatably mounted to the radiolucent sliding member.

15. The surgical table extension of claim 14 wherein the radiolucent mounting structure further comprises a clamp for releasably locking the pivoting member at a desired angular position with respect to the sliding member.

16. The surgical table extension of claim 15 wherein the pivoting member rotates with respect to an axis of rotation substantially parallel to a plane passing through the frame members of the radiolucent skull clamp.

17. The surgical table extension of claim 11 wherein the skull clamp is mounted to the pivoting member.

18. The surgical table extension of claim 17 wherein the skull clamp is pivotally mounted to the pivoting member to rotate about an axis substantially perpendicular to a plane passing through the frame members of the radiolucent skull clamp.

19. A skull clamp for supporting a patient's head comprising:

a first frame member having
an angular positioning mechanism mounted at one end of the first frame member,
a pin holding member rotatably mounted to the angular positioning mechanism, and
a first arm forming an opposite end of the first frame member, the first arm having a first opening extending therethrough, a second frame member having a pin holder on one end thereof, the second frame member having
a first arm forming an opposite end of the second frame member, the first arm having a second opening extending therethrough,
the first arms of the first and second frame members being positionable with respect to each other so that the first and second openings are disposed adjacent each other and the first and second frame members form a generally C-shaped skull clamp; and a mounting clamp extending through the openings of the first arms of the first and second frame members and adapted to removably connect the skull clamp to a supporting structure.

20. A skull clamp for supporting a patient's head comprising:

a first frame member having
an angular positioning mechanism mounted at one end of the first frame member,
a pin holding member rotatably mounted to the angular positioning mechanism, and
a first arm forming an opposite end of the first frame member, the first arm having an opening extending therethrough, a second frame member having a pin holder on one end thereof, the second frame member having
a first arm forming an opposite end of the second frame member, the first arm having an opening extending therethrough, the opening in the first arm of the second frame member having a length permitting the second frame member to be moved through a full range of motion with respect to the first frame member without the second frame member interfering with the clamp;
the first arms of the first and second frame members being positionable with respect to each other so that the first and second frame members form a generally C-shaped skull clamp; and a clamp extending through the openings of the first arms of the first and second frame members and adapted to removably connect the skull clamp to a supporting structure.

21. The skull clamp of claim 20 wherein the clamp is a knob attached to a threaded shaft: the opening in the first arm of the first frame member is a clearance hole for receiving the shaft and the opening in the first arm of the second frame member is a clearance slot for receiving the shaft.

22. The skull clamp of claim 20 wherein the first arm of the first frame member has two opposed side walls with an opening therebetween for receiving the first arm of the second frame member, and each of the side walls has a respective clearance hole for receiving the shaft.

23. A method of mounting a radiolucent skull clamp having a connector to a support having a mating connector, the skull clamp having first and second frame members supporting pin holders at respective first ends and having respective opposite ends positioned with respect to each other so that the first and second frame members form a generally C-shaped skull clamp, the method comprising:

holding the connector of the radiolucent skull clamp against the connector of the support in a desired orientation;

inserting a clamp shaft through a clearance hole extending through the opposite end of the first frame member of the skull clamp;

inserting the clamp shaft through a clearance slot extending through the opposite end of the second frame member of the skull clamp; and securing the clamp shaft to the support, thereby mounting the skull clamp to the support.

24. A method of mounting a radiolucent skull clamp having a connector to a radiolucent support having a mating connector comprising:

holding the connector of the radiolucent skull clamp against the connector of the radiolucent support in a desired orientation;

inserting a radiolucent clamp shaft through a clearance hole in a first side wall of a first frame member of the radiolucent skull clamp;

inserting the radiolucent clamp shaft through a clearance slot in a second radiolucent frame member of the radiolucent skull clamp;

inserting the radiolucent clamp shaft through a clearance hole in a second side wall of the first frame member of the radiolucent skull clamp, the second frame member being movable with respect to the first frame member without contacting the clamp shaft;

securing the clamp shaft to the radiolucent support to securely attach the radiolucent skull clamp to the radiolucent support without impeding relative motion between the first and second frame members.

* * * * *